(12) United States Patent
Kolter et al.

(10) Patent No.: US 7,510,729 B2
(45) Date of Patent: Mar. 31, 2009

(54) COMBINATION OF POLYVINYL ACETATE WITH WATER-INSOLUBLE, ACID-INSOLUBLE, OR ALKALI-INSOLUBLE POLYMERS USED FOR THE PRODUCTION OF FILM COATINGS WITH HIGHLY CONTROLLED RELEASE AND HIGH STABILITY

(75) Inventors: Karl Kolter, Limburgerhof (DE); Roland Bodmeier, Berlin (DE); Andriy Dashevskiy, Berlin (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 646 days.

(21) Appl. No.: 10/507,607

(22) PCT Filed: Mar. 11, 2003

(86) PCT No.: PCT/EP03/02455

§ 371 (c)(1),
(2), (4) Date: Sep. 14, 2004

(87) PCT Pub. No.: WO03/075898

PCT Pub. Date: Sep. 18, 2003

(65) Prior Publication Data

US 2005/0106252 A1   May 19, 2005

(30) Foreign Application Priority Data

Mar. 14, 2002  (DE) ................................ 102 11 289

(51) Int. Cl.
  *A61K 9/16*   (2006.01)
  *A61K 9/28*   (2006.01)
  *A61K 9/30*   (2006.01)
  *A61K 9/32*   (2006.01)
  *A61K 9/34*   (2006.01)
  *A61K 9/36*   (2006.01)
  *A61K 9/42*   (2006.01)

(52) U.S. Cl. ........................ 424/490; 424/474; 424/475; 424/476; 424/479; 424/481; 424/482; 424/491; 424/493; 424/494; 424/496; 424/498

(58) Field of Classification Search ................ None
See application file for complete search history.

(56) References Cited

U.S. PATENT DOCUMENTS

| | | | | |
|---|---|---|---|---|
| 2,852,433 | A * | 9/1958 | Hiatt | ........................... 424/480 |
| 4,629,620 | A * | 12/1986 | Lindahl et al. | ............... 424/473 |
| 4,874,546 | A * | 10/1989 | Yoshida et al. | ......... 252/299.61 |
| 5,102,668 | A * | 4/1992 | Eichel et al. | ................. 424/490 |
| 5,175,003 | A | 12/1992 | Goldman | |
| 5,202,128 | A * | 4/1993 | Morella et al. | ............... 424/469 |
| 6,046,277 | A | 4/2000 | Kolter et al. | |
| 6,576,260 | B2 * | 6/2003 | Ziegler et al. | ............... 424/469 |
| 2001/0007680 | A1 | 7/2001 | Kolter et al. | |

FOREIGN PATENT DOCUMENTS

| | | |
|---|---|---|
| EP | 287 536 | 10/1988 |
| EP | 342 522 | 11/1989 |
| EP | 438 249 | 7/1991 |
| EP | 587 182 | 3/1994 |
| WO | 97/02020 | 1/1997 |
| WO | WO9702020 A1 * | 1/1997 |
| WO | 99/01129 | 1/1999 |
| WO | 01/15668 | 3/2001 |
| WO | 01/80829 | 11/2001 |
| WO | WO 0180829 A2 * | 11/2001 |

* cited by examiner

*Primary Examiner*—S. Tran
(74) *Attorney, Agent, or Firm*—Novak Druce + Quigg LLP (57) ABSTRACT

The invention relates to the combination of polyvinyl acetate and water-insoluble, acid-insoluble, or alkali-insoluble polymers used for producing film coatings for forms of administration in which agents are released in a controlled manner, and methods for the production thereof. The controlled-release properties can be specifically adjusted by means of said combinations, resulting in films having excellent mechanical stability and storage stability. In particular, agents are released independent of the pH by means of the inventive forms of administration.

19 Claims, 9 Drawing Sheets

COMBINATION OF POLYVINYL ACETATE WITH WATER-INSOLUBLE, ACID-INSOLUBLE, OR ALKALI-INSOLUBLE POLYMERS USED FOR THE PRODUCTION OF FILM COATINGS WITH HIGHLY CONTROLLED RELEASE AND HIGH STABILITY

The present invention relates to the combination of polyvinyl acetate with water-insoluble, acid- or alkali-insoluble polymers for producing film coatings for dosage forms with controlled release of active ingredient, and to a process for the production thereof. It is possible through these combinations to adjust deliberately the controlled-release properties, and films of excellent mechanical stability and storage stability result. In particular, the dosage forms of the invention show pH-independent release of active ingredient.

Dosage forms with delayed release of active ingredient must meet very strict requirements since, because the dose of active ingredient is higher than in rapid-release forms, there is a very much greater potential danger of very sudden and rapid release of active ingredient. If large amounts of active ingredient are released and absorbed in a short time it is possible for overdosages with corresponding side effects and even toxic effects to occur. This problem arises in particular with medicinal substances having a relatively narrow therapeutic range. Very different reasons are possible for changes in the release of active ingredient. Thus, cracks and pores in the film coating may form, caused on the one hand by swelling of the core, but also on the other hand by stresses in the coating. Inhomogeneities in the film greatly promote changes in the permeability. These inhomogeneities are attributable to larger or agglomerated powder particles which may derive from abrasion of the core or may be brought about by too rapid drying of the spray suspension. Inhomogeneity of the film coating may also be brought about by non-uniform spraying or the separation/agglomeration of ingredients of the spray dispersion. Film coatings also often adhere very poorly to the substrate and may become detached.

It is moreover understandable that sticking together of the cores during the spraying process followed by tearing apart due to the turbulent or rotational motion of the bed of cores leads to damage in the film coating which cannot be completely eliminated even by application of further layers. This behaviour occurs especially with tacky polymers such as ethyl acrylate/methyl methacrylate copolymer (Eudragit NE 30 D, Kollicoat EMM 30 D). Coated dosage forms must be sufficiently stable for them to withstand both the mechanical stress during the coating process, when the film is still quite moist, and the mechanical stress during further processing, e.g. packing into capsules, when the film is completely dry. There must be no mechanical damage to the film because this would inevitably lead to a great increase in the rate of release of active ingredient.

Particular demands must be met by coated shaped articles which are to be subsequently compressed to tablets which in turn disintegrate into the original coated shaped articles in the stomach after oral administration. The compression step replaces the packing into capsules, and thus a costly process step and the use of animal material (gelatin) are avoided. The release of active ingredient must not be changed by the compression, i.e. the film coating must be plastically deformable and must not be damaged.

Many controlled release polymers such as ethylcellulose or ammonium methacrylate copolymer (ethyl acrylate/methyl methacrylate/trimethylammoniumethyl methacrylate chloride) are very brittle, are poor film-formers and require large amounts of plasticizer. These large amounts of plasticizer are relatively freely available in the film, migrate in the film, migrate out of the film into the core and interact with other ingredients of the dosage form. The result thereof is then also an alteration in the release of active ingredient. The plasticizer concentration in film coatings ought for the stated reasons to be as low as possible. There are as yet no satisfactory solutions for this problem.

The solubility of numerous medicinal substances is pH-dependent, and therefore conventional slow-release forms show pH-dependent release. Medicinal substances are usually weak bases or weak acids or salts thereof. A hydrochloride of a weak base usually has higher solubility at acidic pH, whereas an acid or the alkali metal salt of an acid is more soluble in the neutral or alkaline range. Release of active ingredient is usually fastest at the pH at which the solubility of the active ingredient is greatest, because the concentration gradient from the inside to the outside of the film is then greatest. There have been various attempts to solve this problem, but to date they have all been unsatisfactory and, in some cases, have serious disadvantages.

EP 0438249 describes a naproxen formulation which is coated with a plurality of layers of a combination of a water-insoluble and a water-soluble polymer. The claimed water-soluble polymers show no pH-dependence of the solubility and are therefore unable to control the diffusion according to the solubility of the active ingredient. The application of this multilayer membrane is moreover very complicated and associated with the use of organic solvents. A further special feature is that, besides the active ingredient, a relatively large amount of an organic acid is incorporated into the core, with a corresponding reduction in the active ingredient concentration. The coated particles are then compressed with uncoated ones to give tablets. Overall, this production process is very time-consuming and associated with high costs.

U.S. Pat. No. 5,175,003 describes controlled release pellets with acid-soluble medicinal substances, where the coating consists of a combination of an enteric polymer with a water-soluble polymer. The enteric polymer greatly slows release in the acidic range. In the neutral or alkaline range, the coating disintegrates or completely dissolves. No deliberate control of release by the coating is therefore possible in this range. In addition, in patients having little gastric acid or taking appropriate medicaments to buffer gastric acid, and accordingly having a relatively high pH in the stomach, the coating rapidly dissolves and thus there is then negligible slowing of release.

EP 0287536 describes pharmaceutical coated quinidine formulations with slow release which are characterized in that they display a particular release profile. The coating consists of a combination of hydroxypropylmethylcellulose phthalate (70 to 35%) with insoluble polymers such as ethylcellulose or ethyl acrylate/methyl methacrylate/trimethylammoniumethyl methacrylate copolymer (30 to 65%). Polyvinyl acetate is not mentioned at all. The coating must moreover be applied from organic solution, which involves the known numerous disadvantages such as danger of explosion, toxicity, high costs etc. The described coatings are exceptionally brittle and do not withstand mechanical stress.

PCT 99/01129 claims a process for producing a controlled release form which is suitable for administration of a dihydropyridine calcium antagonist in liquid form. This entails microgranules being coated with a plurality of layers of different polymers. The first layer is a lipophilic pH-insensitive layer, and the others consist alternately of hydrophilic and lipophilic ingredients. It is easy to understand that such a structure is very complicated, application takes a long time and the overall production and thus also the dosage form is very costly. The inventors were apparently unable to find a simpler structure.

The coated pharmaceutical composition described in WO 01/15668 comprises a heterogeneous coating of at least 75% of a water-insoluble polymer and 1 to 25% of an enteric polymer which is able to control release in such a way that there is slowing in an acidic medium and speeding up in a neutral or alkaline medium. Release by the coating is thus not pH-independent but pH-dependent. The water-insoluble polymer may be a quaternary ammonium methacrylate polymer, an acrylic ester copolymer, a methacrylic ester copolymer or a cellulose ether or ester, with ethylcellulose being particularly preferred. Polyvinyl acetate is not mentioned at all in this case. It is possible to use as enteric polymer for example cellulose acetate phthalate, hydroxypropylcellulose acetate phthalate, polyvinyl acetate phthalate or methacrylate copolymer. The rapid release in a neutral or alkaline medium probably derives from the fact that the mixture is, as described by the inventors, heterogeneous, and areas with a high content of enteric polymer are present in the film and rapidly dissolve. The active ingredient then diffuses very rapidly from these to the outside.

Since the water-insoluble polymers mentioned are poor film-formers or tacky, the coating process is very complicated. The described coatings are very brittle and do not withstand mechanical stress. Even the usual stresses occurring during mixing and bottling result in cracks which lead to changes in the release. Because of their brittleness, the claimed film coatings are also unable to withstand swelling processes of the core without damage. Such swelling processes cannot be avoided because active ingredients and virtually all pharmaceutical excipients used for producing cores absorb and take up water, causing an increase in volume. Polymers which are poor film formers, of which ethylcellulose is precisely one, additionally cause inadequate homogeneity of the film, i.e. there is subsequent film formation in the coating even during storage, usually reducing the release. In addition, the high concentrations of plasticizers are a great disadvantage for the stability, because the plasticizers may migrate into the core and also evaporate, markedly altering the film properties and core properties.

U.S. Pat. No. 5,202,128 also describes preparations with pH-dependent release and with the abovementioned disadvantages.

EP-A 868 912 discloses coating materials composed of 10 to 95% by weight of polyvinyl acetate and 5 to 90% by weight of an N-vinylpyrrolidone-containing polymer.

EP-A 1 110 544 discloses the use of a film coating consisting of polyvinyl acetate and hydrophilic additives as taste-masking coating for oral dosage forms, the forms essentially showing rapid release.

It is an object of the present invention to find film coatings which avoid the disadvantages described.

We have found that this object is achieved by dosage forms which are provided with a film coating and have controlled, pH-independent release, where the film coating comprises (A) 10-99% by weight of polyvinyl acetate,
(B) 1-50% by weight of at least one polymer selected from the group consisting of lipophilic water-insoluble polymers, acid-insoluble polymers and alkali-insoluble polymers, and
(C) 0-50% by weight of other pharmaceutically acceptable aids, and the total of components (A), (B) and (C) is 100% by weight.

Combination of polyvinyl acetate with acid-insoluble or alkali-insoluble polymers allows deliberate adjustment of the permeability properties of the coating, so that a pH-independent release results. For this purpose, in the case of an active ingredient which is more soluble at acidic pH there is use of an acid-insoluble polymer which reduces the permeability of the coating in the acidic range but increases it in the alkaline range, where the solubility of the medicinal substance is low. In the case of active ingredients which are more soluble in the alkaline range, an alkali-insoluble polymer is employed. Solubility of the active ingredient and permeability of the coating must always behave in a contrary way. The ratio of polyvinyl acetate to acid-insoluble or alkali-insoluble polymer depends on the solubility differences of the active ingredient at various pH values, i.e. the greater the difference, the more acid-insoluble or alkali-insoluble polymer must be used. The upper limit for this application is at a ratio of approximately 50:50. The normal polyvinyl acetate:acid-insoluble or alkali-insoluble polymer ratios are between 99:1 and 70:30. If the concentrations of acid- or alkali-insoluble polymers used are too high, the integrity of the film coating is no longer ensured at all pH values, and the release again proceeds in a pH-dependent manner.

Acid-insoluble polymers which can be employed are polymers selected from the group consisting of acrylate/methacrylic acid copolymers, carboxyalkylcelluloses, cellulose acetate phthalates, cellulose acetate succinates, cellulose acetate trimellitates, hydroxyalkylcellulose phthalates, hydroxyalkylcellulose acetate succinates, vinyl acetate phthalates. Particularly suitable polymers from these classes are ethyl acrylate/methacrylic acid copolymer, methyl methacrylate/methacrylic acid copolymer, cellulose acetate phthalate, cellulose acetate trimellitate, hydroxypropylmethylcellulose acetate phthalate, hydroxypropylmethylcellulose acetate succinate and polyvinyl acetate phthalate. It is also possible additionally to use shellac.

Polymers insoluble in the neutral and alkaline range which can be used are: basic acrylate or methacrylate copolymers such as, for example, dimethylaminoethyl methacrylate/methyl methacrylate/butyl methacrylate terpolymer or basic polysaccharides such as, for example, chitosan.

Many of the release-slowing polymers and enteric polymers are very brittle, giving rise to the problems described at the outset. It has now been found, surprisingly, that the film properties are considerably improved by additions of polyvinyl acetate. There is a disproportionately large increase in flexibility, thus avoiding fissuring and premature release or dose dumping. The plasticizer content can be reduced. This makes the drug form more stable on storage. In addition, the layer thickness can be reduced, while the properties are improved, resulting in considerable savings of time and costs. In contrast to pure ethylcellulose, a film consisting of a 1:1 ethylcellulose/polyvinyl acetate mixture displays good flexibility.

Shaped articles coated with the polymer combinations with polyvinyl acetate can be compressed together with conventional tableting ingredients such as, for example, microcrystalline cellulose to tablets which rapidly disintegrate again in the stomach to the coated shaped articles. Their release is unexpectedly virtually unchanged compared with the uncompressed pellets.

The combinations of the invention surprisingly make it possible to produce in a simple manner dosage forms with very controlled release and with high mechanical stability, little sensitivity to external influences, high storage stability, excellent appearance, high reproducibility and great drug safety. Thus, the dosage forms coated according to the invention withstand a friability test for 60 min, with the dosage forms falling from a height of 15.5 cm 1500 times, without any effect on the release.

The range of variation in the releases from different individual shaped articles or dosage forms, and the range of variation between different batches, is unexpectedly very low.

The release can be adjusted by the choice and amount of the appropriate polymeric partner in the combination, the combination being chosen so that release is independent of the chosen release medium or the gastric or intestinal fluid. This achieves a more uniform effect of the medicament in the human body.

The ratio of the partners in the combination depends crucially on the solubility differences of the medicinal substance in gastric fluid and in intestinal fluid. If the differences are large, it is also necessary to use a larger amount of polymers with pH-dependent solubility. If they are small, a smaller amount is sufficient.

The coated shaped articles may also be subjected to further processing associated with shear, tensile and compressive stresses without the properties being changed. In addition, the polymer combinations of the invention are extremely resistant to environmental influences such as moisture and oxygen.

A particular advantage of the polymer combination of the invention is that no organic solvents need to be used. Although organic solvents can be employed alone or else in combination with water, the same film properties are achieved even with purely aqueous preparations.

Suitable water-insoluble lipophilic polymers are ethylcellulose, ethyl acrylate/methyl methacrylate copolymer, ethyl acrylate/methyl methacrylate/trimethylammoniumethyl methacrylate chloride copolymer, vinyl acetate/alkyl acrylate or vinyl acetate/alkyl methacrylate copolymer.

The coating can also be applied in two or more layers which differ in their ratio of polyvinyl acetate to lipophilic, water-insoluble or acid-insoluble or alkali-insoluble polymers. Polyvinyl acetate-rich and -poor layers are thus applied.

The coating can also be applied in two or more layers, one comprising polyvinyl acetate and the other comprising the lipophilic, water-insoluble or acid-insoluble or alkali-insoluble polymer. Although it is likewise possible in this case to use polyvinyl acetate in the inner layer, there are certain advantages to using polyvinyl acetate as outer layer. Because of the interaction at the interface of the two layers, they adhere very strongly to one another and cannot be separated from one another.

If the coating is to have two or more layers, the coating suspensions are sprayed consecutively.

The particular interaction of polyvinyl acetate with cellulose derivatives and acrylate/methacrylate copolymers is evident not only in the flexibility but also in other film properties. Thus, the roughness of the films is reduced, the gloss is considerably enhanced and the tackiness is reduced. The resistance to abrasion of the combinations is higher than that of the pure components. These marked improvements are based on a homogeneous film-formation process which generates no weak points in the integrity of the film. This indicates that the improvement in the film properties is partly based on the formation of hydrogen bonds between the hydroxyl groups of the cellulose and the ester structure of the polyvinyl acetate. The carboxyl groups of acid-insoluble polymers can also react with the ester structure in the same way. This interaction is evident from a shift in the carbonyl band of the polyvinyl acetate in infrered spectroscopy.

Mixing of two dispersions together may result in coagulation, but this is not caused by incompatibility of the polymers themselves but is caused by destruction of the principle stabilizing the dispersions. Dispersions are usually electrostatically stabilized, i.e. the dispersion droplets have a negative or positive zeta potential. If this is lowered to near zero, coagulation occurs immediately. This phenomenon is seen with the combination of polyvinyl acetate dispersion (Kollicoat® SR 30 D) and methacrylic acid/ethyl acrylate copolymer dispersion (Kollicoat MAE 30 DP).

It is surprisingly possible to produce excellent films with these components, despite their incompatibility as dispersion, if the two dispersions have been sprayed through separate spray nozzles onto shaped articles. Coagulation of the fine dispersion particles thus takes place directly on the surface on the shaped articles to be coated. Such film coatings show no signs of any separation of polymer constituents; they are smooth, glossy, resistant to abrasion and exceptionally mechanically stable.

Coagulation of dispersions on mixing can also be avoided or at least reduced by addition of surface-active substances. Substances preferably employed for this purpose have an HLB above 10. These surface-active substances may be ionic or nonionic in nature. Those particularly suitable are polyoxyethylene sorbitan fatty acid esters such as, for example, polysorbate 80, polyoxyethylene fatty acids, polyoxyethylene fatty alcohols, ethoxylated castor oil, ethoxylated hydrogenated castor oil such as, for example, Cremophor RH 40, alkali metal salts of fatty acids such as, for example, sodium stearate, alkali metal salts of alkyl sulfates or alkylsulfonates such as, for example, sodium lauryl sulfate, polyoxyethylene/polyoxypropylene block copolymers such as, for example Lutrol F 68 or F 127, sodium dioctyl sulfosuccinate. The usual effective concentrations are between 0.2 and 20%, preferably between 0.5 and 10%.

The coatings may additionally comprise water-soluble substances which may be of low or high molecular weight. It is possible thereby to increase the rate of release of active ingredients which show a poor permeation behavior. These substances either dissolve out of the coating and generate pores or they ensure faster and greater uptake of water by the film coating, likewise increasing the permeation. The pH-independence of release is unaffected thereby. Examples of low molecular weight water-soluble substances are sugars or sugar alcohols such as lactose, sorbitol, mannitol, xylitol, glucose, sucrose, salts of organic or inorganic acids such as sodium chloride, potassium acetate, sodium phosphates, sodium citrates, sodium succinates, sodium tartrates or else urea. Examples of high molecular weight substances which can be employed are: polyvinylpyrrolidone, vinylpyrrolidone/vinyl acetate copolymers, polyvinyl alcohol, hydroxypropylcellulose, hydroxypropylmethylcellulose, cellulose, maltodextrins, galactomannans, dextrins, dextrans, pectins, xanthans, alginates, polydextrose, polyethylene glycols, polyoxyethylene/polyoxypropylene block copolymers.

The described coatings can be applied to a wide variety of cores such as, for example, pellets, crystals, granules, tablets, drug delivery systems.

The dosage forms can be coated in conventional coating equipment such as, for example, horizontal drum coaters, dip coaters, fluidized bed coaters, Kugelcoaters, coating pans. The inlet air temperature can in these cases be between 30 and 100° C., preferably between 50 and 90° C.

The coating preparations to be applied can surprisingly be concentrated to very high solids contents, resulting in a very short and economical spraying process. The solids concentrations are normally set at from 15 to 40%.

Other conventional coating ingredients which can be used are:
- pigments such as, for example, titanium dioxide, iron oxides, lacked dyes, water-soluble dyes
  - suspending excipients
  - adhesion promoters
- non-sticking agents such as, for example, talc, magnesium stearate, stearic acid, microcrystalline cellulose
- plasticizers such as, for example, triethyl citrate, triacetin, propylene glycol, diethyl sebacate, dibutyl phthalate, acetyl tributyl citrate, polyethylene glycol, glycerol monostearate
- antifoams such as, for example silicone emulsions
- surfactants These substances are ordinarily used to provide the coated form with a color or appearance and to improve the handling of the spray suspension and the spraying process.

Because of the good film-forming properties, in principle no curing, i.e. heat treatment of the dosage forms of the invention for a prolonged period, is necessary. In certain cases it may, however, improve the stability of the release of active ingredients on storage.

Active ingredients from all areas of use can be formulated according to the invention. Besides medicaments, it is also possible to produce in this way veterinary medicaments, crop protection agents, food supplements, nutraceuticals, vitamin, carotenoid, trace element and mineral preparations.

The excellent film-forming properties of the preparations of the invention are also evident from the fact that very different shapes of cores can be coated, such as, for example, crystals, granules, pellets, tablets, extrudates, drug delivery systems.

EXAMPLES

Example 1

Two layers were applied to 1.08 kg of acetylsalicylic acid crystals with a particle size of from 0.5 to 0.8 mm in a Glatt GPC G1 fluidized bed coater. The first layer comprised mainly dimethylaminoethyl methacrylate/methyl methacrylate/butyl methacrylate copolymer, while the second layer comprised mainly polyvinyl acetate as film former.

| Coating formula 1 | |
|---|---|
| Dimethylaminoethyl methacrylate/methyl methacrylate/butyl methacrylate terpolymer (Eudragit ® E PO) | 40.0 g |
| Polyvinyl acetate dispersion, 30% by weight in water (Kollicoat SR 30 D) | 50.0 g |
| Talc | 5.0 g |
| Sodium lauryl sulfate | 1.0 g |
| Water | 250.0 g |

| Coating formula 2 | |
|---|---|
| Polyvinyl acetate dispersion, 30% by weight in water (Kollicoat SR 30 D) | 483.3 g |
| Talc | 55.0 g |
| Vinylpyrrolidone/vinyl acetate (6:4) copolymer (Kollidon VA 64) | 7.5 g |
| Sodium lauryl sulfate | 0.5 g |
| Water | 150.0 g |

The ratio of polyvinyl acetate to alkali-insoluble polymer as total of the two layers is 8:2.

Preparation of Spray Suspension 1

Spray suspension 1 was prepared by stirring 40.0 g of Eudragit E PO and 5.0 g of talc with 1.0 g of sodium lauryl sulfate into 250.0 g of water and dispersing finely. 50.0 g of Kollicoat SR 30 D were added to this suspension with stirring.

Preparation of Spray Suspension 2

55.0 g of talc, 7.5 g of Kollidon VA 64 and 0.5 g of sodium lauryl sulfate were likewise stirred into 150.0 g of water with stirring, and this suspension was slowly added to 483.3 g of Kollicoat SR 30 D with stirring.

The two coating suspensions were applied to the crystals in a fluidized bed by means of a Wurster insert at an inlet air temperature of 55° C. and with a spraying rate of 12 g/min. The weight of the coating was 25% of that of the acetylsalicylic acid crystals originally present.

Figure 1:
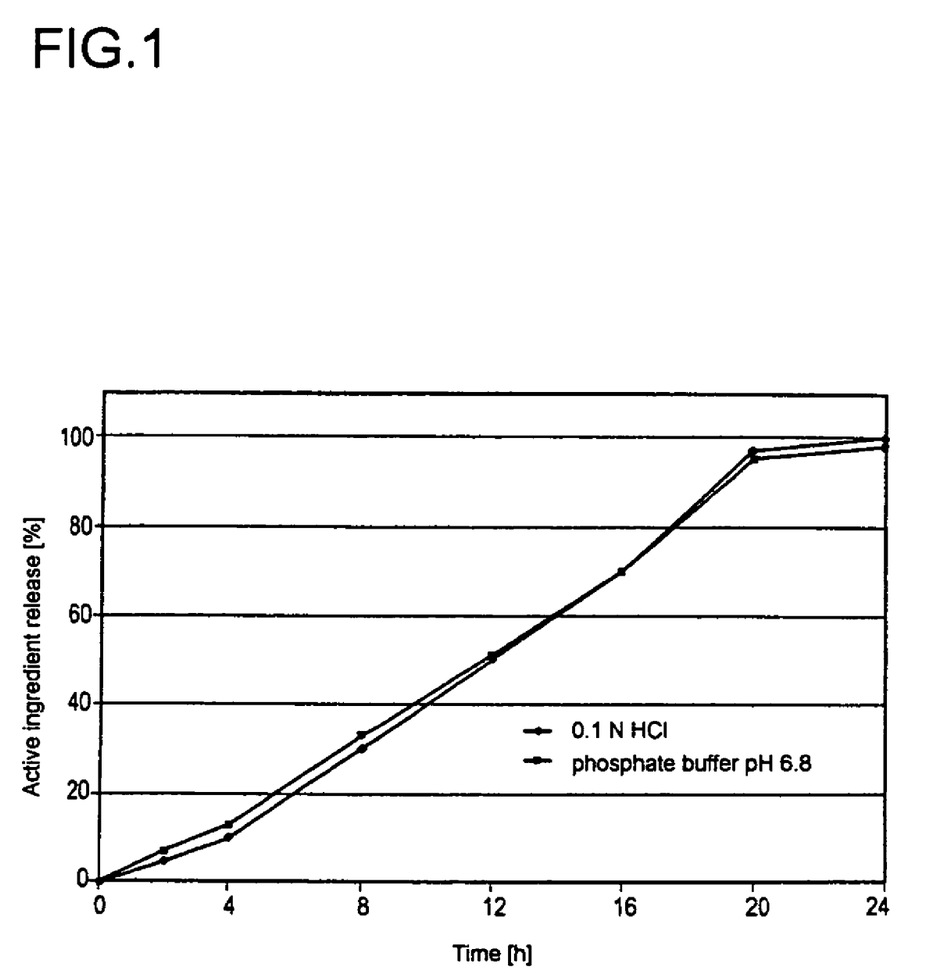

The release of the active ingredient was determined in 0.1 N HCl (simulated gastric fluid ◆) and in phosphate buffer of pH 6.8 (simulated intestinal fluid ■). The release curves are shown in FIG. 1.

Acetylsalicylic acid shows a markedly pH-dependent solubility. It is only 0.45% in the acidic range but is greater than 25% in the neutral and alkaline range.

The release was equally fast in both media.

Comparative Example 1

Dimethylaminoethyl methacrylate/methyl methacrylate/butyl methacrylate terpolymer (Eudragit E PO) was omitted from the formula of Example 1. The coating process was carried out analogously.

Figure 2:
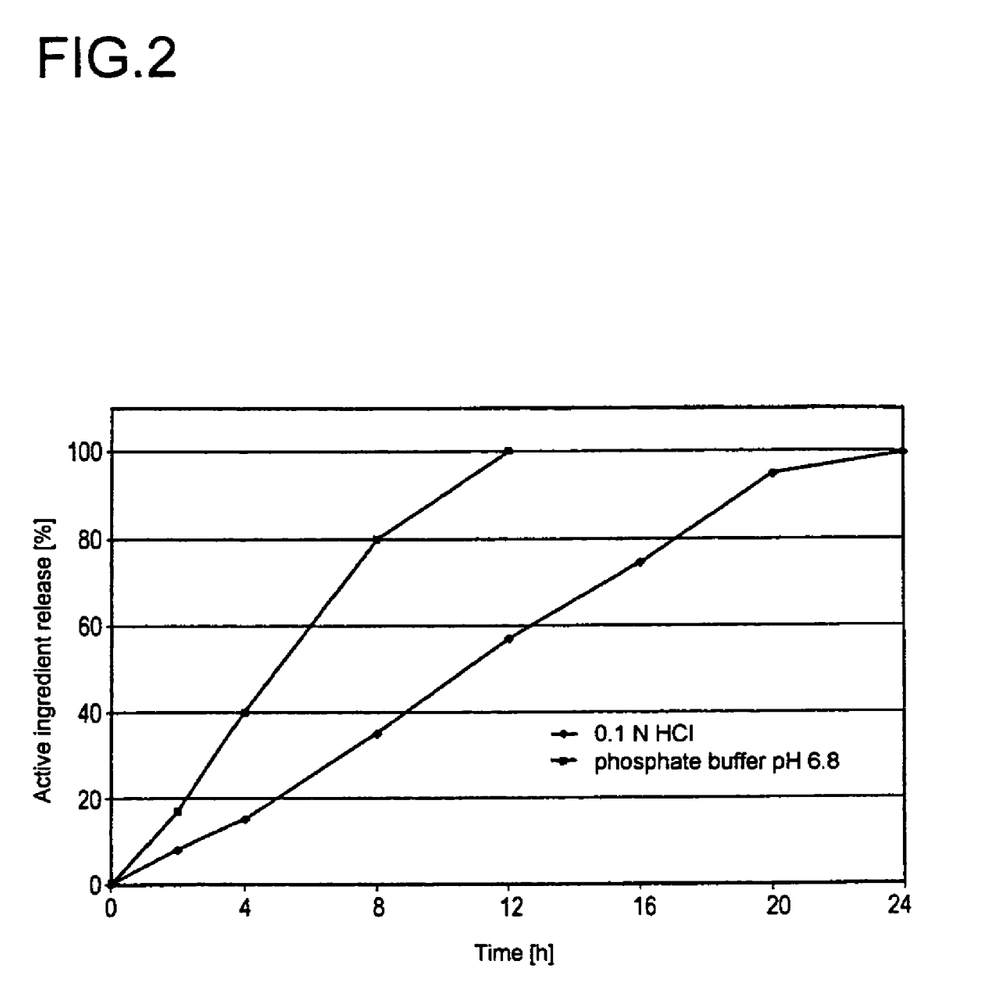

The release was distinctly faster in phosphate buffer of pH 6.8 than in 0.1 N HCl. The release curves are shown in FIG. 2.

Example 2

600 g of acetylsalicylic acid pellets with an active ingredient content of 10% (10% acetylsalicylic acid, 0.5% hydroxypropylmethylcellulose 5 mPas, 0.05% polyethylene glycol 4000, 89.45% sucrose), which had been produced by a drug layering process starting from sucrose beads (sugar spheres), were coated with 2-layer film coating in a Huettlin Kugel coater HKC 5. The first layer consisted of a dimethylaminoethyl methacrylate/methyl methacrylate/butyl methacrylate copolymer coating, while the second layer comprised polyvinyl acetate as film former.

| Coating formula 1 | |
|---|---|
| Dimethylaminoethyl methacrylate/methyl methacrylate/butyl methacrylate terpolymer (Eudragit ® E PO) | 30.0 g |
| Dibutyl sebacate | 4.5 g |
| Talc | 30.0 g |
| Sodium lauryl sulfate | 2.1 g |
| Water | 316.0 g |

| Coating formula 2 | |
|---|---|
| Polyvinyl acetate dispersion, 30% by weight in water (Kollicoat SR 30 D) | 300.0 g |
| Water | 300.0 g |

The ratio of polyvinyl acetate to alkali-insoluble polymer was 7.5:2.5.

Coating Suspension 1

The coating formula was prepared by stirring 30.0 g of Eudragit E PO and 4.5 g of dibutyl sebacate with 1.0 g of sodium lauryl sulfate into 316.0 g of water and finely dispersing. 30.0 g of talc were likewise added and dispersed with stirring.

Coating Suspension 2

300.0 g of polyvinyl acetate dispersion were diluted with 300 g of water.

The coating dispersions was applied to the pellets in a fluidized bed at an inlet air temperature of 50° C. and with a spraying rate of 6 g/min. The product temperature was about 39° C. in both cases.

The weight of film former in the first layer was 5% and in the second layer was 15%.

The release of the active ingredient was determined in 0.1 N HCl (◆) and in phosphate buffer (■) of pH 6.8. Acetylsalicylic acid shows a markedly pH-dependent solubility. It is only 0.45% in the acid range but is above 25% in the neutral and alkaline range.

Figure 3:
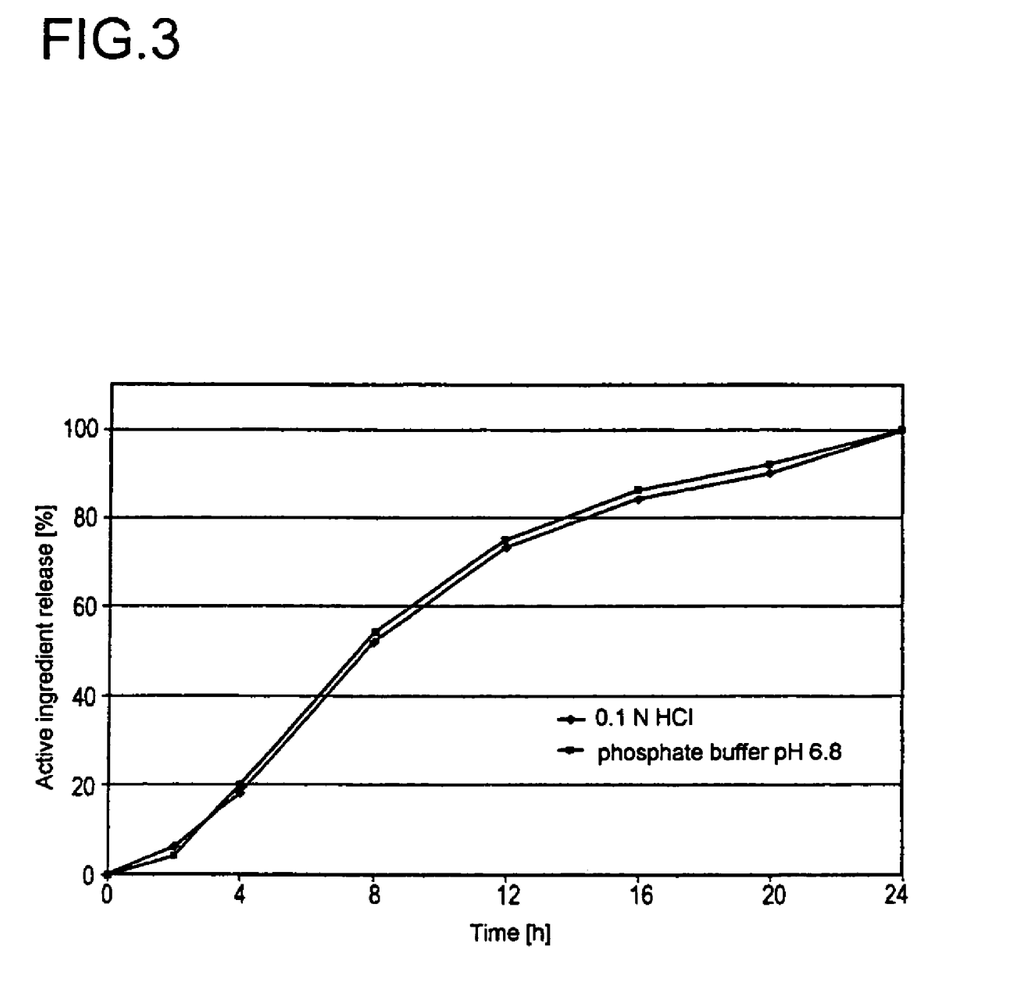

The release was equally fast in both media. The release curves are shown in FIG. 3.

Example 3

0.5 kg of verapamil pellets (consisting of 40% verapamil HCl, 40% microcrystalline cellulose, 15% Ludipress LCE (formulation of 96.5% by weight lactose and 3.5% by weight polyvinylpyrrolidone), 5% vinylpyrrolidone/vinyl acetate (6:4) copolymer) with a particle size of from 0.8 to 1.5 mm was coated with a two-layer coating in an Aeromatic Stream 1 fluidized bed coater. The first layer comprised methacrylic acid/ethyl acrylate copolymer as film-forming polymer, and the second layer comprised polyvinyl acetate.

| Coating suspension 1 | |
|---|---|
| Methacrylic acid/ethyl acrylate copolymer, 30% by weight in water, dispersion (Kollicoat MAE 30 DP) | 50.0 g |
| Triacetin | 2.3 g |
| Polyvinylpyrrolidone of K value 90 | 1.7 g |
| Water | 46.0 g |

| Coating suspension 2 | |
|---|---|
| Polyvinyl acetate dispersion, 30% by weight in water (Kollicoat SR 30 D) | 283.3 g |
| Talc | 10.0 g |
| Triacetin | 4.2 g |
| Water | 200.0 g |

The ratio of polyvinyl acetate to acid-insoluble polymer is 85:15.

Preparation of Coating Suspension 1

2.3 g of triacetin and 1.7 g of polyvinylpyrrolidone K 90 were added with stirring to 26.0 g of water, and mixed with 50.0 g of Kollicoat MAE 30 DP with stirring.

Preparation of Coating Suspension 2

4.2 g of triacetin were dissolved in 200.0 g of water, and 10.0 g of talc were dispersed therein with stirring. This suspension was then slowly added with stirring to 283.3 g of Kollicoat SR 30 D.

The inlet air temperature was 65° C. with coating suspension 1 and 60° C. with coating suspension 2; the spraying rate was 12 g/min. The weight of the coating was 24% of that of the Verapamil pellets.

The release of the active ingredient was determined in 0.1 N HCl (◆) and in phosphate buffer (■) of pH 7.4. Verapamil shows a markedly pH-dependent solubility. It is 7.1% in the acidic range but only 0.2% in the neutral or alkaline range.

Figure 4:
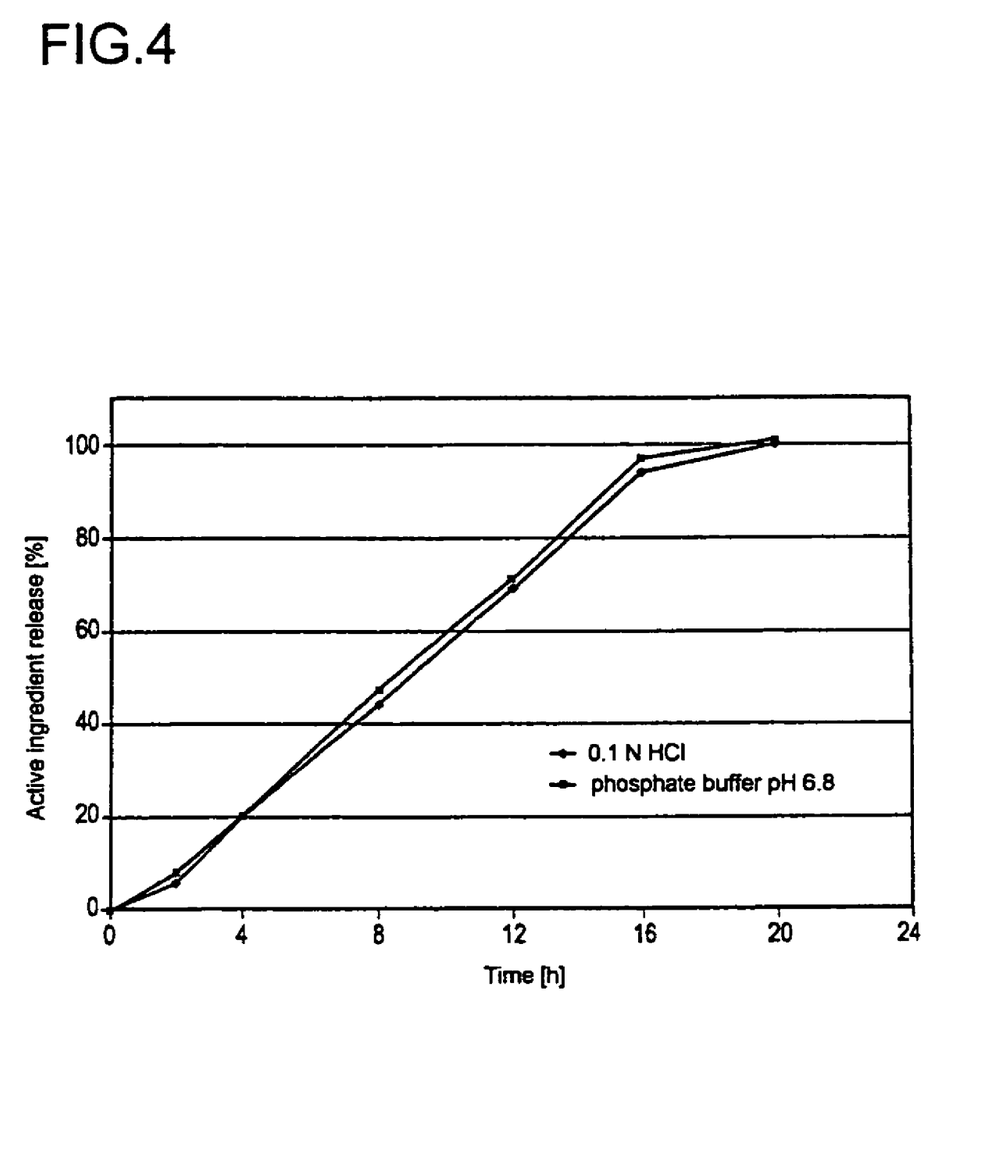

The release curves are shown in FIG. 4.

The release was equally fast in 0.1 N HCl and in phosphate buffer of pH 7.4.

Comparative Example 3

Ethyl acrylate/methacrylic acid copolymer was omitted from the formula of Example 3. The coating process was carried out analogously.

Figure 5:
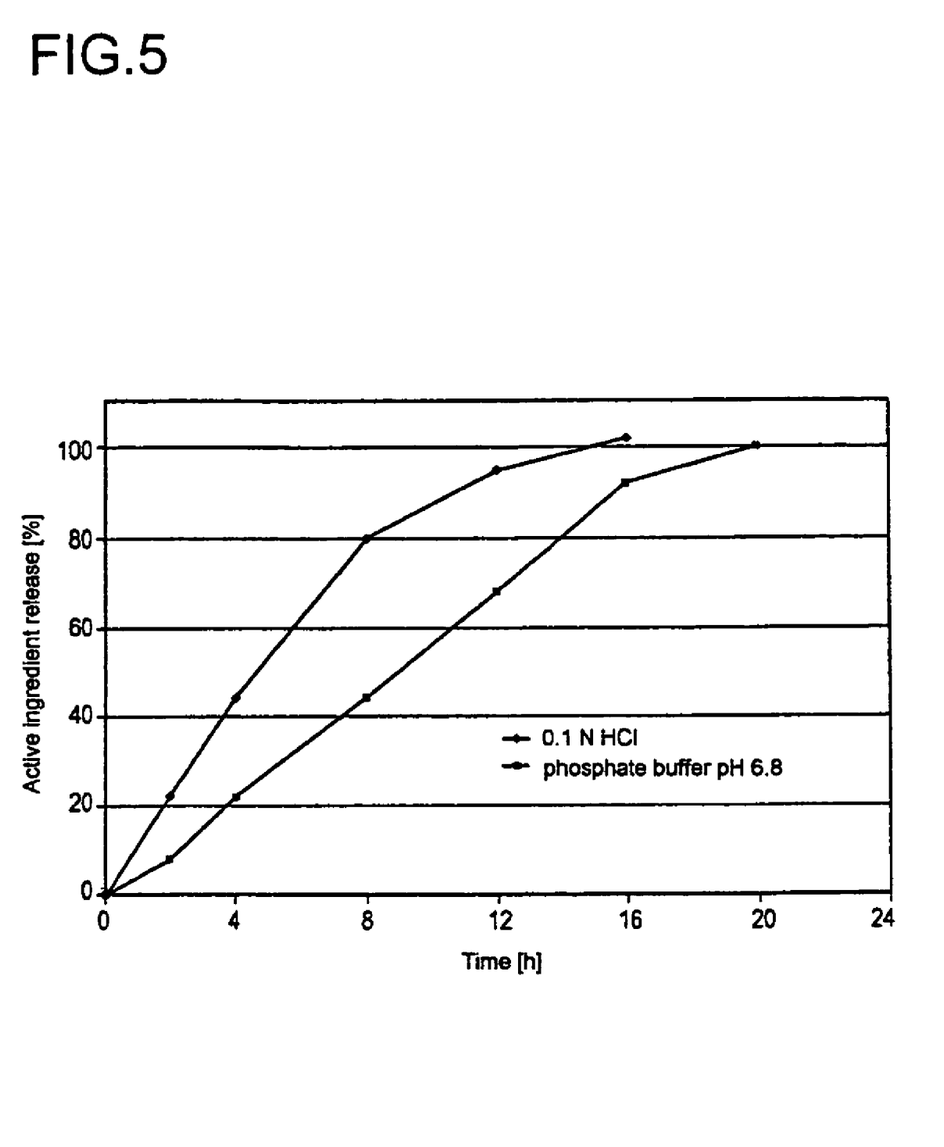

The release was faster in 0.1 N HCl (◆) than in phosphate buffer (■) of pH 7.4. The release curves are shown in FIG. 5.

Example 4

600 g of Verapamil pellets (consisting of 10% Verapamil HCl, 0.5% hydroxypropylmethylcellulose 5 mpas, 0.05% polyethylene glycol 4000, 89.45% sucrose) with a particle size of from 0.8 to 1.5 mm, produced by the drug layering process, were coated simultaneously in a Huettlin Kugelcoater HKC 5 with the following spray suspensions:

| Spray suspension 1 | |
|---|---|
| Polyvinyl acetate dispersion 30% (Kollicoat SR 30 D) | 352.0 g |
| Triethyl citrate | 10.6 g |
| Water | 327.4 g |

| Spray suspension 2 | |
|---|---|
| Methacrylic acid/ethyl acrylate/1:1 dispersion 30% (Kollicoat MAE 30 DP) | 48.0 g |
| Triethyl citrate | 1.4 g |
| Water | 640.6 g |

The ratio of polyvinyl acetate to acid-insoluble polymer is 88:12.

Preparation of the Spray Suspensions:

Triethyl citrate was dissolved in the stated amount of water, and this solution was stirred into the Kollicoat dispersion.

Both dispersions were sprayed in parallel via separate spray nozzles onto the Verapamil pellets in a fluidized bed.

The inlet air temperature was 46° C. and the spraying rate was 6 g/min. The weight of film former, expressed as the total of polyvinyl acetate and methacrylic acid/ethyl acrylate copolymer, was 20% of that of the Verapamil pellets.

The release of the active ingredient was determined in 0.1 N HCl and in phosphate buffer of pH 6.8. Verapamil shows a markedly pH-dependent solubility. It is 7.1% in the acidic range but only 0.2% in the neutral or alkaline range.

Figure 6:
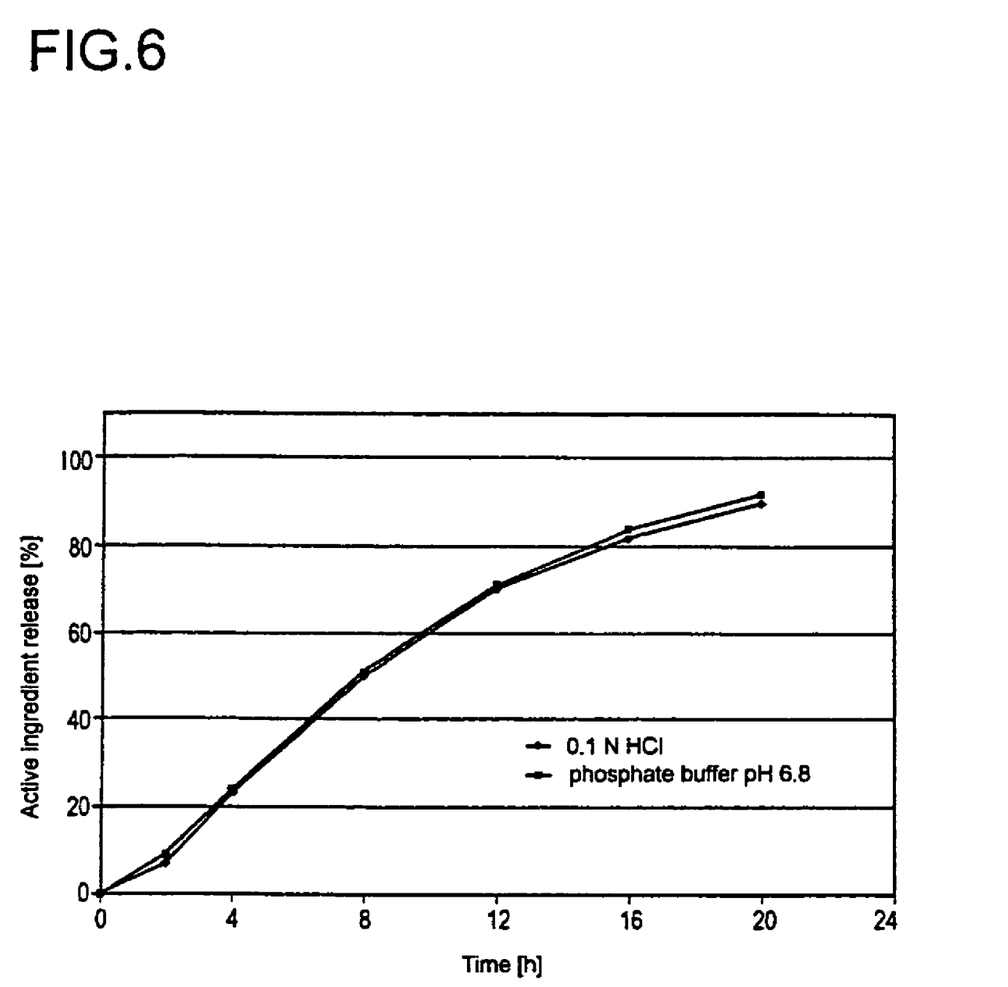

The release was equally fast in 0.1 N HCl (◆) and in phosphate buffer of pH 6.8 (■). The release curves are shown in FIG. 6.

Example 5

0.5 kg of propranolol HCl pellets (20% propranolol HCl, 51.7% microcrystalline cellulose, 25.8% lactose, 2.5% vinylpyrrolidone/vinyl acatate (6:4) copolymer (Kollidon VA 64) with a particle size of from 0.4 to 1.5 mm, produced by wet extrusion and subsequent spheronization, was coated in a Aeromatic Stream 1 fluidized bed coater with the following coating formula:

| | |
|---|---|
| Polyvinyl acetate dispersion 30% (Kollicoat SR 30 D) | 150.0 g |
| Ethylcellulose dispersion 30% (Aquacoat ECD) | 100.0 g |
| Triacetin | 12.5 g |
| Talc | 20.0 g |
| Vinylpyrrolidone/vinyl acetate (6:4) copolymer | 2.5 g |
| Simethicone | 0.5 g |
| Water | 150.0 g |

The ratio of polyvinyl acetate to lipophilic polymer was 3:2.

The coating formula was prepared by stirring and dispersing Kollidon VA 64, triacetin, simethicone and talc in 150.0 g of water. This preparation was mixed with Kollicoat SR 30 D, and then Aquacoat ECD was added.

The coating dispersion was applied to the pellets in a fluidized bed by means of a Wurster insert at an inlet air temperature of 62° C. and with a spraying rate of 12 g/min. The weight of the coating was 22% of that of the propranolol pellets.

The release of the active ingredient was determined in 0.1 N HCl for 2 h and then in phosphate buffer of pH 6.8. The coated pellets were mechanically stressed (12 min Friabilator test, corresponding to 300 revolutions, height of fall 15.5 cm), and the release was again determined.

Figure 7:
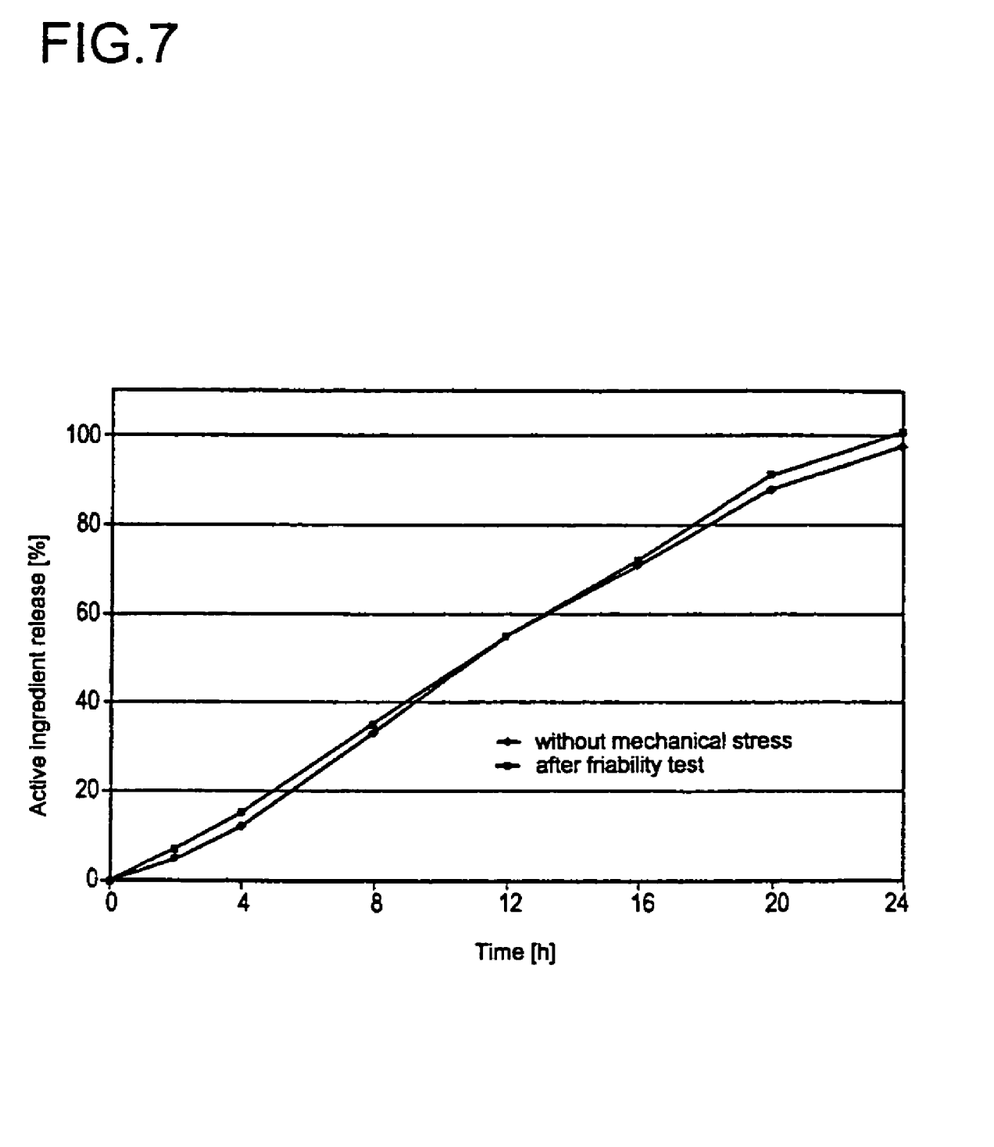

Mechanical stress had no effects on the release. The release curves are shown in FIG. 7 (◆without mechanical stress; ■after friability test).

Comparative Example 5

Polyvinyl acetate was omitted and was replaced by further Aquacoat in the formula of Example 5. The coating process was carried out analogously.

Figure 8:
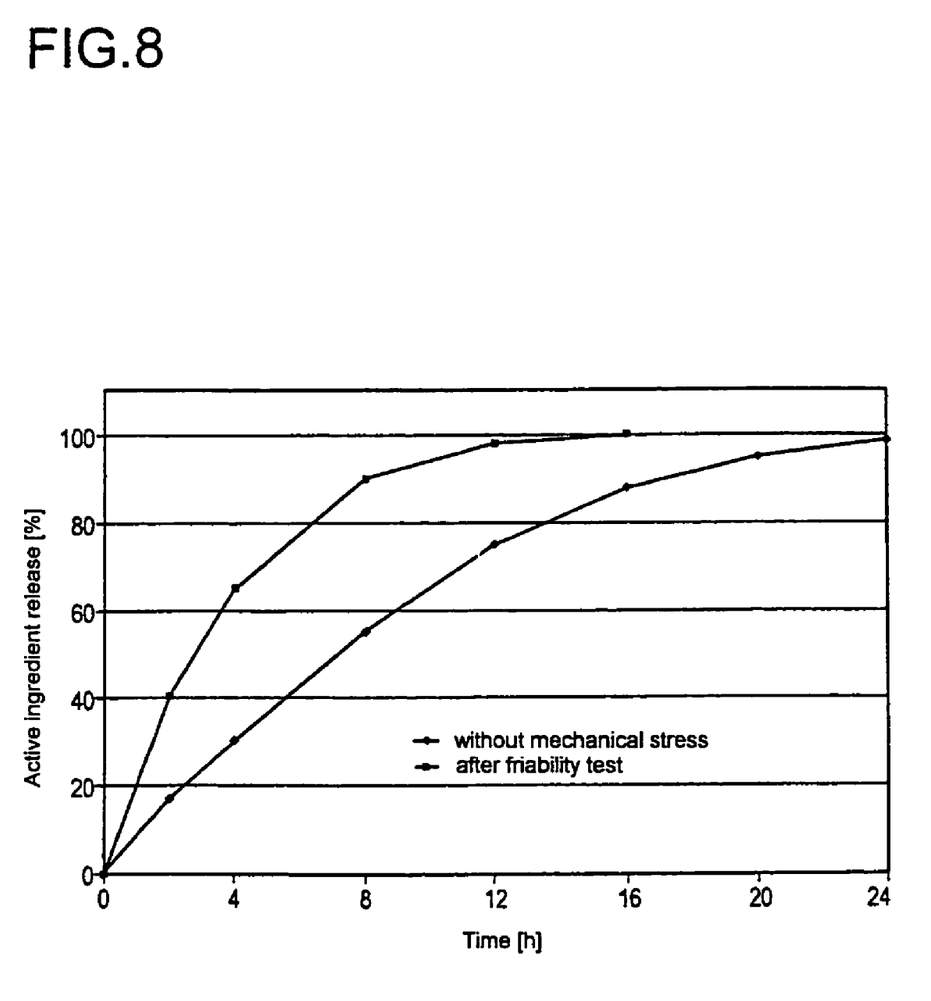

The release after mechanical stress was considerably more rapid. The release curves are shown in FIG. 8 (◆without mechanical stress; ■after friability test).

The pellets from Example 5 and from Comparative Example 5 were additionally compressed to tablets with the following formula and with a diameter of 10 mm and a weight of 400 mg:

| | |
|---|---|
| Coated propranolol pellets | 250.0 g |
| Microcrystalline cellulose | 250.0 g |
| Magnesium stearate | 2.5 g |

Figure 9:
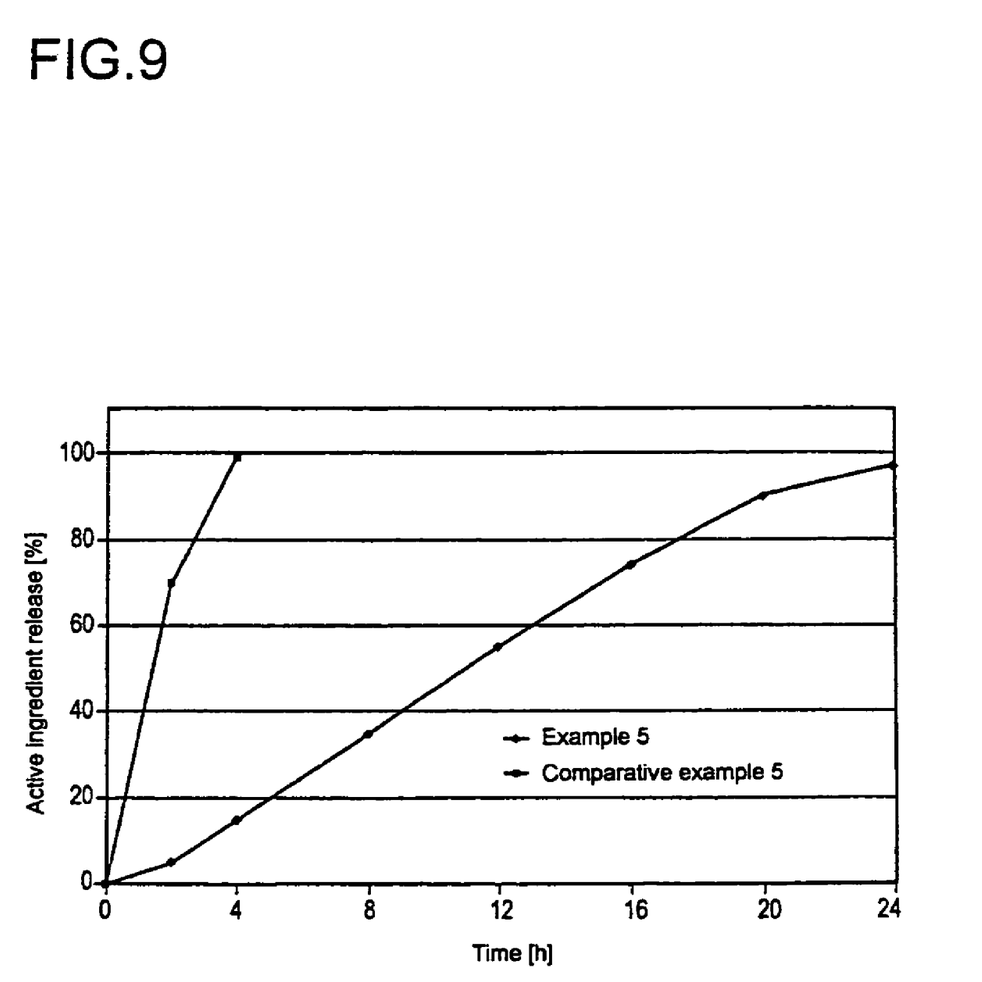

The release was likewise determined on the tablets. The release curves are shown in FIG. 9 (◆compressed from Examples 5; ■compressed pellets from Comparative example 5).

The pellets coated with polyvinyl acetate/ethylcellulose show slow release even after compression, whereas those coated only with ethylcellulose show a distinctly faster release.

The following table indicates the release of active ingredient as shown in FIGS. 1 to 9 in [%].

TABLE

Release of active ingredient in [%]

| Time [h] | Simulated gastric fluid (0.1 N HCl) | Simulated intestinal fluid (phosphate buffer pH 6.8) | FIG. No. |
|---|---|---|---|
| 0 | 0 | 0 | 1 |
| 2 | 5 | 7 | |
| 4 | 10 | 13 | |
| 8 | 30 | 33 | |
| 12 | 50 | 51 | |
| 16 | 70 | 70 | |
| 20 | 97 | 95 | |
| 24 | 100 | 98 | |
| 0 | 0 | 0 | 2 |
| 2 | 8 | 17 | |
| 4 | 15 | 40 | |
| 8 | 35 | 80 | |
| 12 | 57 | 100 | |
| 16 | 75 | — | |
| 20 | 95 | — | |
| 24 | 100 | — | |
| 0 | 0 | 0 | 3 |
| 2 | 6 | 4 | |
| 4 | 18 | 20 | |
| 8 | 52 | 54 | |
| 12 | 73 | 75 | |
| 16 | 84 | 86 | |
| 20 | 90 | 92 | |
| 24 | 100 | 100 | |
| 0 | 0 | 0 | 4 |
| 2 | 6 | 8 | |
| 4 | 20 | 20 | |
| 8 | 44 | 47 | |
| 12 | 69 | 71 | |
| 16 | 94 | 97 | |
| 20 | 100 | 101 | |
| 24 | — | — | |
| 0 | 0 | 0 | 5 |
| 2 | 22 | 8 | |
| 4 | 44 | 22 | |
| 8 | 80 | 44 | |
| 12 | 95 | 68 | |
| 16 | 102 | 92 | |
| 20 | — | 100 | |
| 24 | — | — | |
| 0 | 0 | 0 | 6 |
| 2 | 7 | 9 | |
| 4 | 23 | 24 | |
| 8 | 50 | 51 | |
| 12 | 70 | 71 | |

We claim:

1. An active ingredient-containing dosage form which is provided with a film coating and has controlled, pH-independent release, where the film coating has a thickness of between 20 and 200 μm and comprises
   (A) 10-99% by weight of polyvinyl acetate,
   (B) 1-50% by weight of at least one polymer selected from the group consisting of lipophilic water-insoluble polymers, acid-insoluble polymers and alkali-insoluble polymers, and
   (C) 0-50% by weight of other pharmaceutically acceptable aids, the total of components (A), (B) and (C) is 100% by weight and the ratio of (A) to (B) is from 70:30 to 99:1.

2. A dosage form as claimed in claim 1, where the lipophilic water-insoluble polymers are selected from the group consisting of alkylcelluloses, acrylate/methacrylate copolymers, vinyl acetate/methacrylate and vinyl acetate/acrylate copolymers.

3. A dosage form as claimed in claim 1, where the acid-insoluble polymers are selected from the group consisting of acrylate/methacrylic acid copolymers, carboxyalkylcelluloses, cellulose acetate phthalates, cellulose acetate succinates, cellulose acetate trimellitates, hydroxyalkylcellulose phthalates, hydroxyalkylcellulose acetate succinates, vinyl acetate phthalates and vinyl acetate succinates.

4. A dosage form as claimed in claim 1, where the alkali-insoluble polymers are selected from the group consisting of basic acrylate/methacrylate copolymers and basic natural polysaccharides.

5. A dosage form as claimed in claim 1, where the film coating comprises 20 to 80% by weight of polymers (A) and 5 to 40% by weight of polymers (B).

6. A dosage form as claimed in claim 1, where ethylcellulose, ethyl acrylate/methyl methacrylate copolymer and ethyl acrylate/methyl methacrylate/trimethylammoniumethyl methacrylate chloride terpolymer or mixtures thereof are employed as lipophilic water-insoluble polymer.

7. A dosage form as claimed in claim 1, where ethyl acrylate/methacrylic acid copolymer, methyl methacrylate/ methacrylic acid copolymer, methyl methacrylate/methyl acrylate/ methacrylic acid copolymer, carboxymethylcellulose, cellulose acetate phthalate, hydroxypropylmethylcellulose phthalate, hydroxypropylmethylcellulose acetate phthalate, hydroxypropylmethylcellulose acetate succinate, polyvinyl acetate phthalate, shellac and mixtures thereof are employed as acid-insoluble polymer.

8. A dosage form as claimed in claim 1, where dimethylaminoethyl methacrylate/methyl methacrylate/butyl methacrylate terpolymer, chitosan or mixtures thereof are employed as alkali-insoluble polymer.

9. A dosage form as claimed in claim 1, where the polyvinyl acetate has a molecular weight of from 10 000 to 2 000 000.

10. A dosage form as claimed in claim 1, where polyvinyl acetate and, where appropriate, the lipophilic, water-insoluble or acid-insoluble or alkali-insoluble polymers are employed in the form of an aqueous dispersion for producing the film coating.

11. A dosage form as claimed in claim 1, where all the film coating ingredients are mixed before production of the film coating, where appropriate with the addition of a surface-active substance.

12. An active ingredient-containing dosage form which is provided with a film coating and has controlled, pH-independent release, where the film coating has a thickness of between 20 and 200 μm and comprises
(A) 10-99% by weight of polyvinyl acetate,
(B) 1-50% by weight of at least one polymer selected from the group consisting of lipophilic water-insoluble polymers, acid-insoluble polymers and alkali-insoluble polymer, and
(C) 0-50% by weight of other pharmaceutically acceptable aids,
the total of components (A), (B) and (C) is 100% by weight and the ratio of (A) to (B) is from 70:30 to 99:1
wherein polyvinyl acetate and the lipophilic, water-insoluble or acid-insoluble or alkali-insoluble polymers are applied in two or more layers which differ in their ratio of polyvinyl acetate to lipophilic, water-insoluble or acid-insoluble or alkali-insoluble polymers.

13. A dosage form as claimed in claim 1, where polyvinyl acetate and the lipophilic, water-insoluble or acid-insoluble or alkali-insoluble polymers are applied in two or more layers, one comprising polyvinyl acetate and the other comprising the lipophilic water-insoluble or acid-insoluble or alkali-insoluble polymer.

14. A dosage form as claimed in claim 1, where the film coating additionally comprises hydrophilic, water-soluble polymers or low molecular weight, water-soluble substances.

15. A dosage form as claimed in claim 1, in the form of pellets, granules, crystals, extrudates, tablets or drug delivery systems.

16. A dosage form as claimed in claim 1, which comprises medicinal substances, veterinary medicinal substances, vitamins, carotenoids, nutraceuticals, food supplements or additives, minerals, trace elements or crop protection agents as active ingredients.

17. A tablet produced by compression of the coated dosage form as claimed in claim 1 together with conventional pharmaceutical excipients.

18. A process for preparing the dosage forms of the invention as claimed in claim 1, which comprises an aqueous film coating preparation being sprayed onto shaped articles in motion and simultaneously being dried by input of hot air, where polyvinyl acetate and the lipophilic water-insoluble or acid-insoluble or alkali-insoluble polymers are applied through separate spray nozzles in the coating device.

19. A dosage form as claimed in claim 9, where the polyvinyl acetate has a molecular weight of from 100 000 to 1 000 000.

* * * * *